United States Patent
O'Sullivan

(10) Patent No.: US 8,273,016 B2
(45) Date of Patent: Sep. 25, 2012

(54) ESOPHAGUS ISOLATION DEVICE

(75) Inventor: Martin F. O'Sullivan, Long Beach, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 465 days.

(21) Appl. No.: 11/372,665

(22) Filed: Mar. 10, 2006

(65) Prior Publication Data
US 2007/0225701 A1   Sep. 27, 2007

(51) Int. Cl.
A61B 1/267 (2006.01)
A61M 31/00 (2006.01)
A61M 37/00 (2006.01)
A61M 25/00 (2006.01)

(52) U.S. Cl. .................. 600/190; 604/95.04; 604/528

(58) Field of Classification Search .............. 600/434, 600/435, 585, 194; 604/95.04, 523–532
See application file for complete search history.

(56) References Cited

U.S. PATENT DOCUMENTS

| | | | |
|---|---|---|---|
| 4,898,591 A | | 2/1990 | Jang et al. |
| 5,037,391 A | * | 8/1991 | Hammerslag et al. ........ 604/528 |
| 5,104,393 A | | 4/1992 | Isner et al. |
| RE34,502 E | | 1/1994 | Webster, Jr. |
| 5,391,199 A | | 2/1995 | Ben-Haim |
| 5,427,119 A | | 6/1995 | Swartz et al. |
| 5,443,489 A | | 8/1995 | Ben-Haim |
| 5,480,422 A | | 1/1996 | Ben-Haim |
| 5,487,385 A | | 1/1996 | Avitall |
| 5,497,774 A | | 3/1996 | Swartz et al. |
| 5,546,951 A | | 8/1996 | Ben-Haim |
| 5,558,091 A | | 9/1996 | Acker et al. |
| 5,558,665 A | * | 9/1996 | Kieturakis ................ 606/1 |
| 5,564,440 A | | 10/1996 | Swartz et al. |
| 5,570,671 A | | 11/1996 | Hickey |
| 5,575,766 A | | 11/1996 | Swartz et al. |
| 5,582,609 A | | 12/1996 | Swanson et al. |
| 5,617,854 A | | 4/1997 | Munsif |

(Continued)

FOREIGN PATENT DOCUMENTS

EP    0 970 718 A2    1/2000

(Continued)

OTHER PUBLICATIONS

Extended European Search Report dated May 18, 2007, issued to European Application No. 07250922.7 (5 pages).

Primary Examiner — Kevin T Truong
Assistant Examiner — David Bates
(74) Attorney, Agent, or Firm — Christie, Parker & Hale, LLP

(57) ABSTRACT

An esophagus isolation catheter for deflecting an esophagus of a patient away from an ablation site in the left atrium of the patient's heart is provided. The catheter comprises an elongated catheter body and a deflectable section. In one embodiment, the catheter comprises a deflectable intermediate section mounted at the distal end of the catheter body and a generally straight tip section mounted at the distal end of the intermediate section. In this embodiment, the catheter comprises two puller wires, one anchored proximal the other. The intermediate section deflects to form a generally C-shaped curve. In an alternative embodiment, the catheter comprises a deflectable tip section mounted at the distal end of the catheter body. In this embodiment, the catheter comprises only one puller wire. The tip section carries a tip electrode having an atraumatic design to prevent damage to the esophagus upon deflection.

31 Claims, 16 Drawing Sheets

U.S. PATENT DOCUMENTS

| | | | |
|---|---|---|---|
| 5,674,197 A * | 10/1997 | van Muiden et al. | 604/95.04 |
| 5,681,344 A * | 10/1997 | Kelly | 606/194 |
| 5,897,529 A | 4/1999 | Ponzi | |
| 6,198,974 B1 * | 3/2001 | Webster, Jr. | 607/122 |
| 6,285,898 B1 | 9/2001 | Ben-Haim | |
| 6,371,955 B1 | 4/2002 | Fuimaono et al. | |
| 6,468,260 B1 | 10/2002 | Bumbalough et al. | |
| 6,475,214 B1 | 11/2002 | Moaddeb | |
| 6,477,396 B1 | 11/2002 | Mest et al. | |
| 6,733,499 B2 | 5/2004 | Scheib | |
| 7,235,070 B2 * | 6/2007 | Vanney | 606/41 |
| 2002/0087089 A1 | 7/2002 | Ben-Haim | |
| 2003/0045871 A1 | 3/2003 | Jain et al. | |
| 2003/0078494 A1 | 4/2003 | Panescu et al. | |
| 2004/0097801 A1 | 5/2004 | Mesallum | |
| 2004/0162572 A1 * | 8/2004 | Sauer | 606/170 |
| 2004/0193239 A1 | 9/2004 | Falwell et al. | |
| 2005/0131508 A1 | 6/2005 | Garabedian et al. | |
| 2005/0143770 A1 * | 6/2005 | Carter et al. | 606/170 |
| 2006/0106375 A1 | 5/2006 | Werneth et al. | |
| 2006/0116576 A1 | 6/2006 | McGee et al. | |
| 2006/0252993 A1 * | 11/2006 | Freed et al. | 600/146 |
| 2007/0118105 A1 * | 5/2007 | Miller | 606/41 |

FOREIGN PATENT DOCUMENTS

| | | |
|---|---|---|
| WO | WO 93/20767 | 10/1993 |
| WO | WO 96/26672 | 9/1996 |
| WO | WO 2006/044794 A2 | 4/2006 |
| WO | WO 2006/055286 A2 | 5/2006 |

* cited by examiner

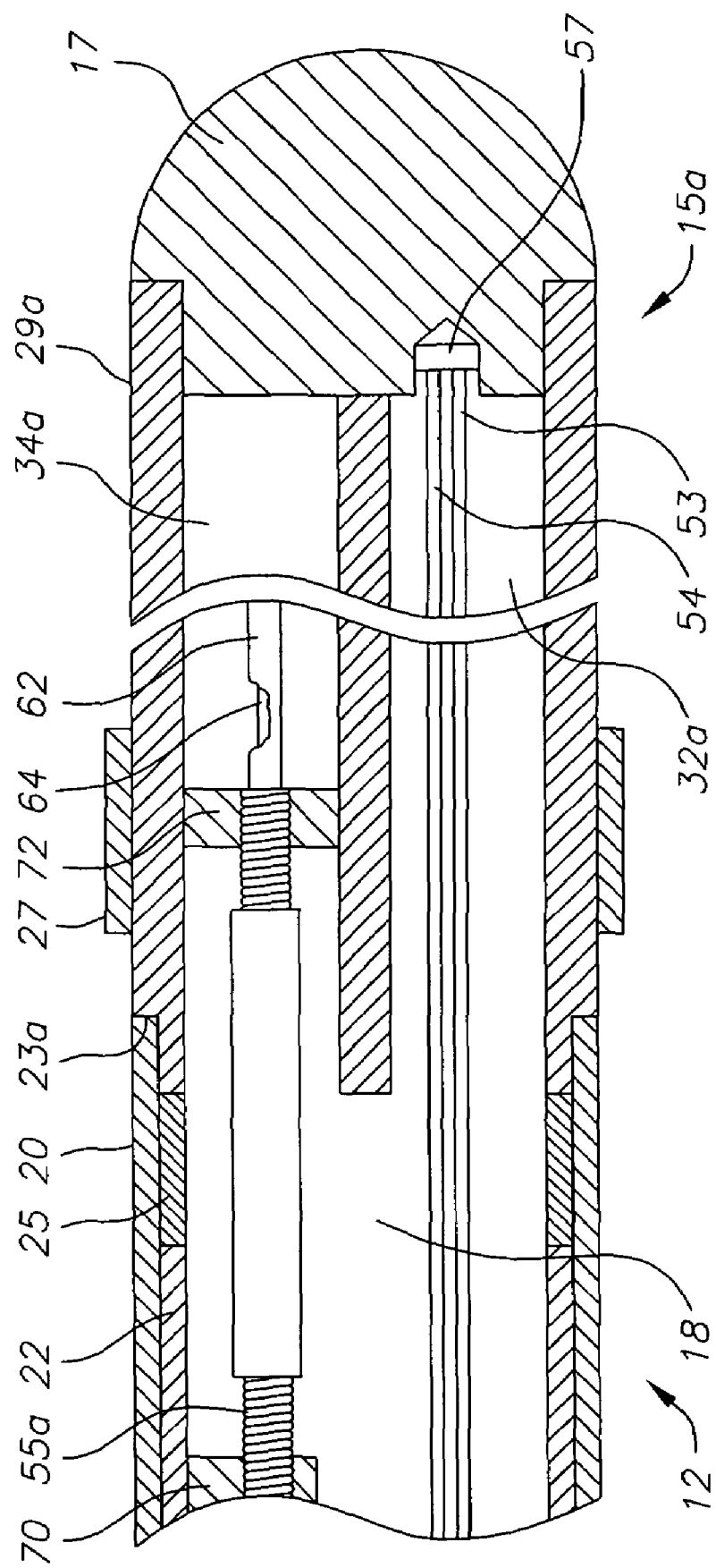

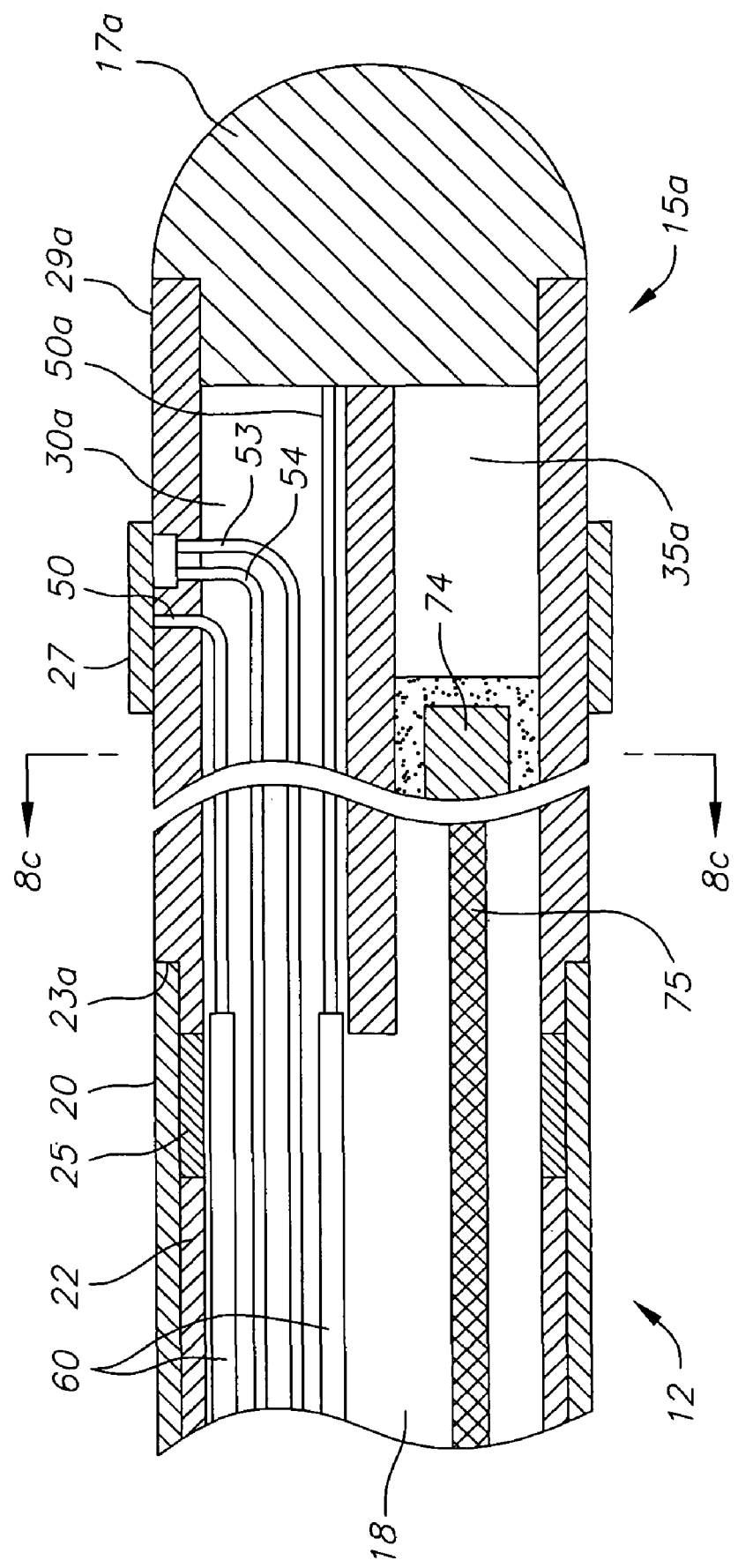

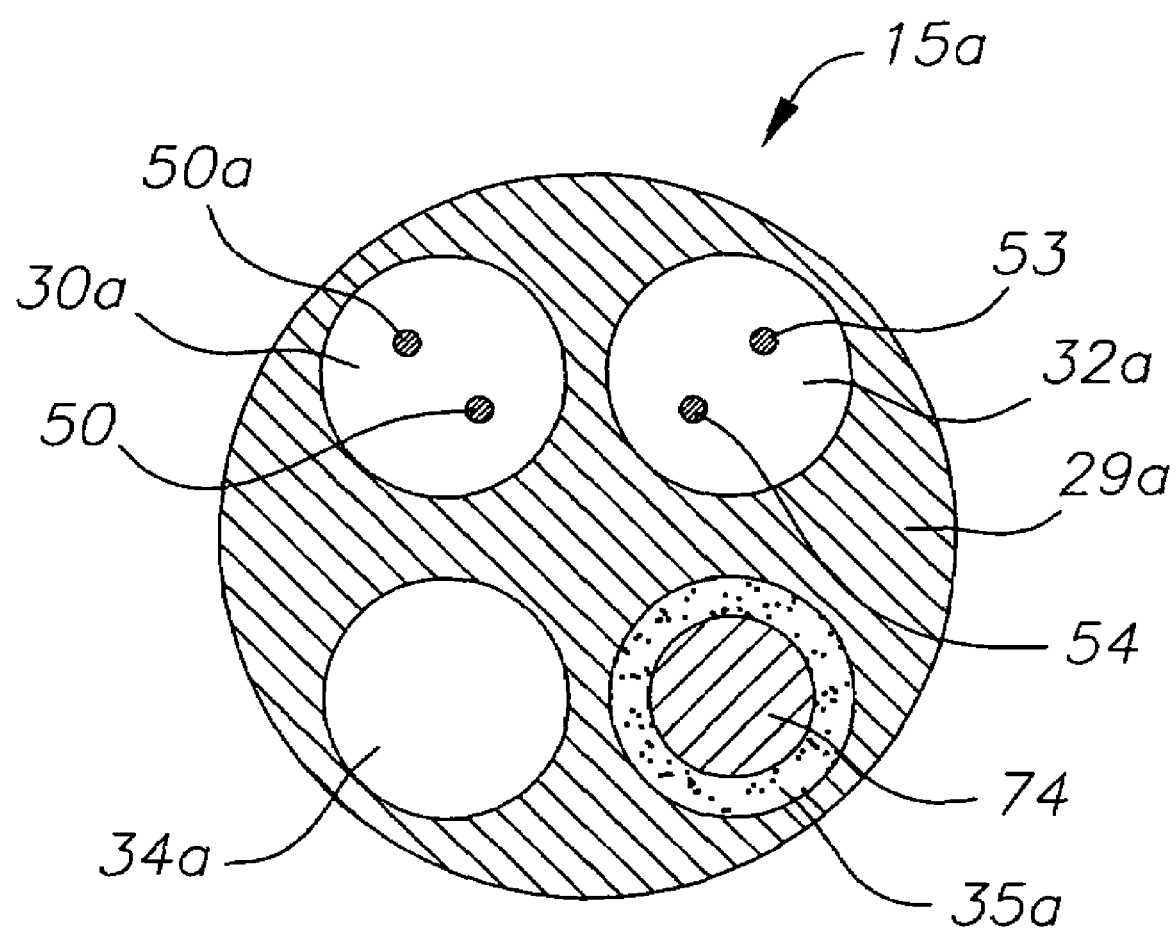

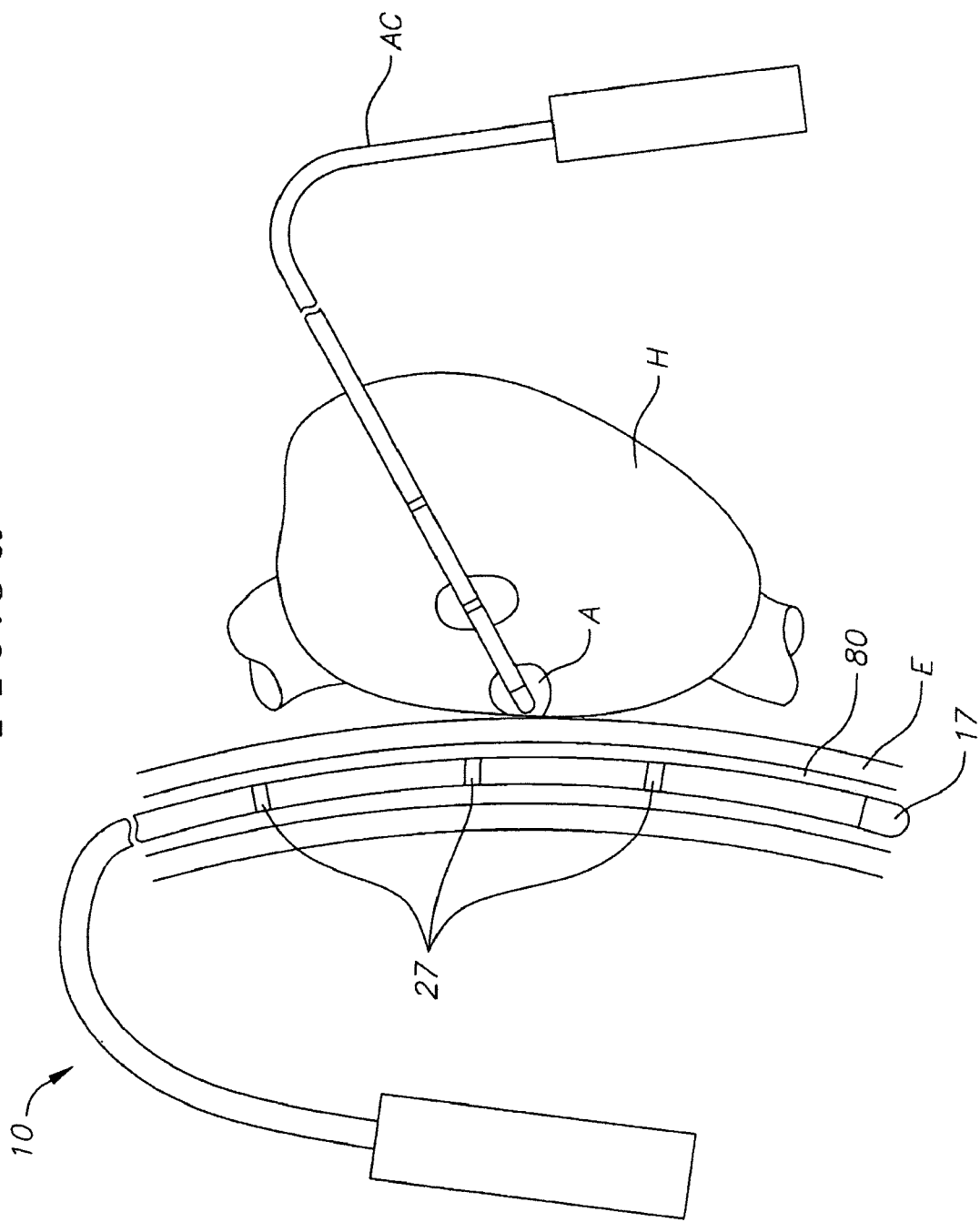

ESOPHAGUS ISOLATION DEVICE

FIELD OF THE INVENTION

This invention is directed to a device for deflecting the esophagus in a direction away from an ablation site within the heart.

BACKGROUND OF THE INVENTION

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, although such pharmacological solutions are not generally believed to be entirely effective in many cases, and may in some cases result in proarrhythmia and long term inefficacy. Several surgical approaches have also been developed with the intention of treating atrial fibrillation. One particular example is known as the "maze procedure." In general, the maze procedure is designed to relieve atrial arrhythmia by restoring effective atrial systole and sinus node control through a prescribed pattern of incisions about the tissue wall. In the early clinical experiences reported, the maze procedure included surgical incisions in both the right and the left atrial chambers. However, more recent reports predict that the surgical maze procedure may be substantially efficacious when performed only in the left atrium.

The maze procedure, as performed in the left atrium, generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction of the atrial arrhythmia by creating conduction blocks within the aberrant electrical conduction pathways.

While the maze procedure has met with some success in treating patients with atrial arrhythmia, its highly invasive methodology is believed to be prohibitive in most cases. However, these procedures have provided a guiding principle that mechanically isolating faulty cardiac tissue may successfully prevent atrial arrhythmia, and particularly atrial fibrillation caused by perpetually wandering reentrant wavelets or focal regions of arrhythmogenic conduction.

Success with surgical interventions through atrial segmentation, particularly with regard to the surgical maze procedure just described, has inspired the development of less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as those disclosed in U.S. Pat. No. 5,617,854 to Munsif, U.S. Pat. No. 4,898,591 to Jang, et al., U.S. Pat. No. 5,487,385 to Avitall, and U.S. Pat. No. 5,582,609 to Swanson, the disclosures of which are incorporated herein by reference. The use of particular guiding sheath designs for use in ablation procedures in both the right and left atrial chambers are disclosed in U.S. Pat. Nos. 5,427,119, 5,197,119, 5,497,774, 5,564,440 and 5,575,766 to Swartz et al., the entire disclosures of which are incorporated herein by reference. In addition, various energy delivery modalities have been disclosed for forming such atrial wall lesions, and include use of microwave, laser and more commonly, radiofrequency energies to create conduction blocks along the cardiac tissue wall, as disclosed in WO 93/20767 to Stem, et al., U.S. Pat. No. 5,104,393 to Isner, et al. and U.S. Pat. No. 5,575,766 to Swartz, et al., respectively, the entire disclosures of which are incorporated herein by reference.

The success of catheter based ablation procedures has led to numerous improvements to the catheters used for the procedures. However, the traumatic nature of the ablation procedure has given rise to certain complications. One such complication is the possibility of damaging the esophagus, which lies very close to, and often touches the outer wall of the left atrium. Damage to the esophagus is sometimes caused when the esophagus touches or is close to the tissue in the left atrium that is being ablated. The heat from the ablation procedure may penetrate through the tissue of the left atrium and reach the esophagus. This damage to the esophagus is extremely dangerous, as the damaged esophagus often becomes infected. The damage to the esophagus often manifests as a fistula, or hole, that develops over time. This hole causes any infection to spread to the heart wall. This damage carries an extremely high mortality rate. Accordingly, a need exists for a device that deflects the esophagus away from the heart wall during an ablation procedure.

SUMMARY OF THE INVENTION

The present invention is directed to an esophagus isolation catheter having an elongated catheter body and a deflectable section. In one embodiment, the catheter comprises a deflectable intermediate section and a generally straight tip section.

In this embodiment, the catheter comprises two puller wires, one anchored in the distal end of the intermediate section, and the other anchored in the proximal end of the intermediate section. Longitudinal movement of the puller wires results in deflection of the intermediate section.

The tip section is mounted at the distal end of the intermediate section and is long enough so that when the intermediate section is deflected, the tip section does not deflect. In such an arrangement, the deflected intermediate section forms a generally C-shaped curve with the tip section, and deflects the esophagus away from an ablation site in the left atrium of a heart.

In an alternative embodiment, the catheter comprises a deflectable tip section. In this embodiment, the intermediate section is omitted, and the catheter comprises only one puller wire. The puller wire is anchored near the center of the tip section. The distal section of the tip section, distal the anchor point of the puller wire is sufficiently long such that upon deflection, the distal section of the tip section remains substantially straight, resulting in a substantially C-shaped curve. The tip section carries a tip electrode having an atraumatic design to prevent damage to the esophagus upon deflection.

In either of the above embodiments, the catheter further comprises one or more radiopaque markers disposed along the deflectable section. The radiopaque markers are used to position the deflectable section over the ablation site. The radiopaque markers may comprise ring electrodes made at least partially of a radiopaque material.

The catheter may also further comprise one or more temperature sensors to enable monitoring of the temperature within the esophagus. Such temperature monitoring enables the physician to control the power delivered to the ablation electrode during an ablation procedure to prevent thermal damage to the esophagus.

In addition, an electromagnetic sensor may be anchored within the deflection section. The sensor is used to record the location of the esophagus before, during and after the ablation procedure.

In use, the catheter is inserted into the esophagus of a patient either directly or within a gastric tube. The deflectable section is then deflected to direct the esophagus away from the ablation site. After deflection of the esophagus, the ablation procedure is performed.

BRIEF DESCRIPTION OF THE DRAWINGS

These and other features and advantages of the present invention will be better understood by reference to the following detailed description when considered in conjunction with the accompanying drawings wherein:

FIG. 8a is a side cross-sectional view of the catheter body of the catheter of FIG. 7, including the junction between the catheter body and tip section;

FIG. 8b is a side cross-sectional view, taken of the side opposite that of FIG. 8a, of the catheter body of the catheter of FIG. 8a, including the junction between the catheter body and tip section;

FIG. 8c is a longitudinal cross-sectional view of the tip section of FIG. 8b, taken along line 8c-8c;

FIG. 9a is an exaggerated schematic depicting a catheter in a straight configuration in an esophagus according to one embodiment of the invention;

FIG. 9b is an exaggerated schematic depicting posterior deflection of the catheter of FIG. 9a; and FIG. 9c is an exaggerated schematic depicting lateral deflection of the catheter of FIG. 9a.

DETAILED DESCRIPTION OF THE INVENTION

Figure 1:
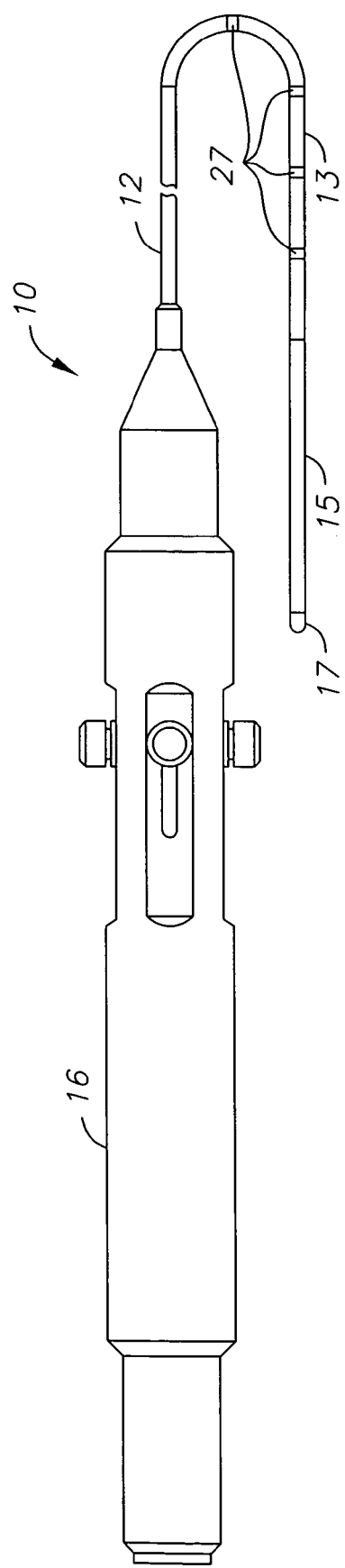
FIG. 1 is an elevated side view of an esophagus isolation catheter according to one embodiment of the present invention.

In one exemplary embodiment of the present invention, there is provided an esophagus isolation catheter 10 having a deflectable section. As shown in FIG. 1, one embodiment of the esophagus isolation catheter 10 generally comprises an elongated catheter body 12 having an axis and proximal and distal ends, an intermediate section 13 mounted at the distal end of the catheter body 12, a tip section 15 mounted at the distal end of the intermediate section 13, and a control handle 16 mounted at the proximal end of the catheter body 12.

The catheter body 12 comprises an elongated tubular construction having a single central lumen 18. It will be understood, however, that the catheter body 12 may comprise more than one lumen as desired. The catheter body 12 is flexible, i.e., bendable, but substantially non-compressible along its length. The catheter body 12 can be of any suitable construction and made of any suitable material. One exemplary construction comprises an outer wall 20 made of polyurethane or PEBAX. Alternatively, the outer wall 20 is made of a suitable silicone, silicone-based, or silicone-containing material. The outer wall 20 can comprise an embedded braided mesh of stainless steel or the like to increase torsional stiffness of the catheter body 12 so that when the control handle 16 is rotated, the intermediate section 13 and the tip section 15 rotate in a corresponding manner.

The overall length and diameter of the catheter 10 may vary as desired. One exemplary catheter has an overall length of about 48 inches. The outer diameter of the catheter body 12 is not critical, but should be no more than about 8 french. The inner surface of the outer wall 20 may be lined with a stiffening tube 22, which can be made of any suitable material, for example nylon or polyimide. The stiffening tube 22, along with the braided outer wall 20, provides improved torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. One exemplary catheter has an outer diameter of about 0.092 inch and a lumen diameter of about 0.052 inch.

Figure 4A:
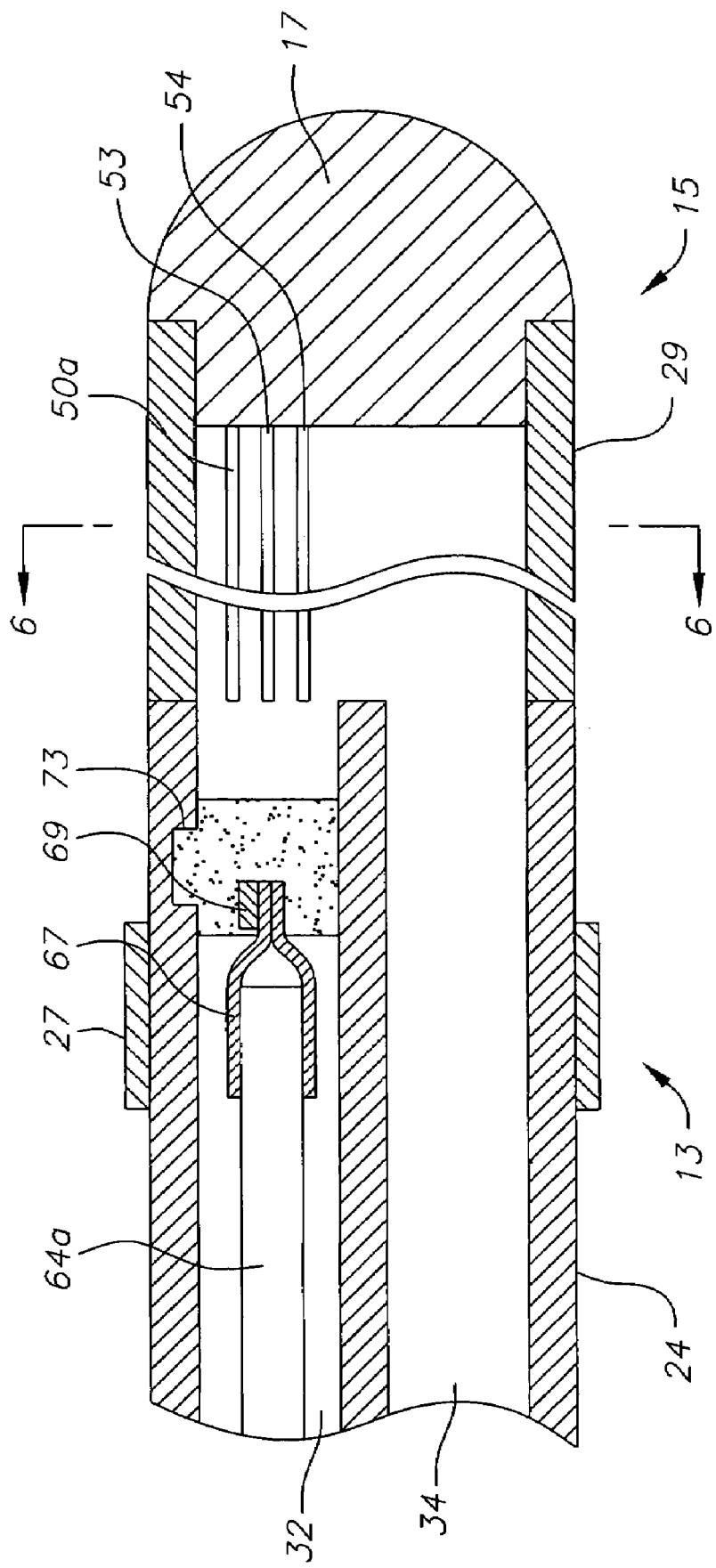
FIG. 4a is a side cross-sectional view of a tip section according to one embodiment of the present invention, including the junction between the intermediate section and the tip section.
Figure 4B:
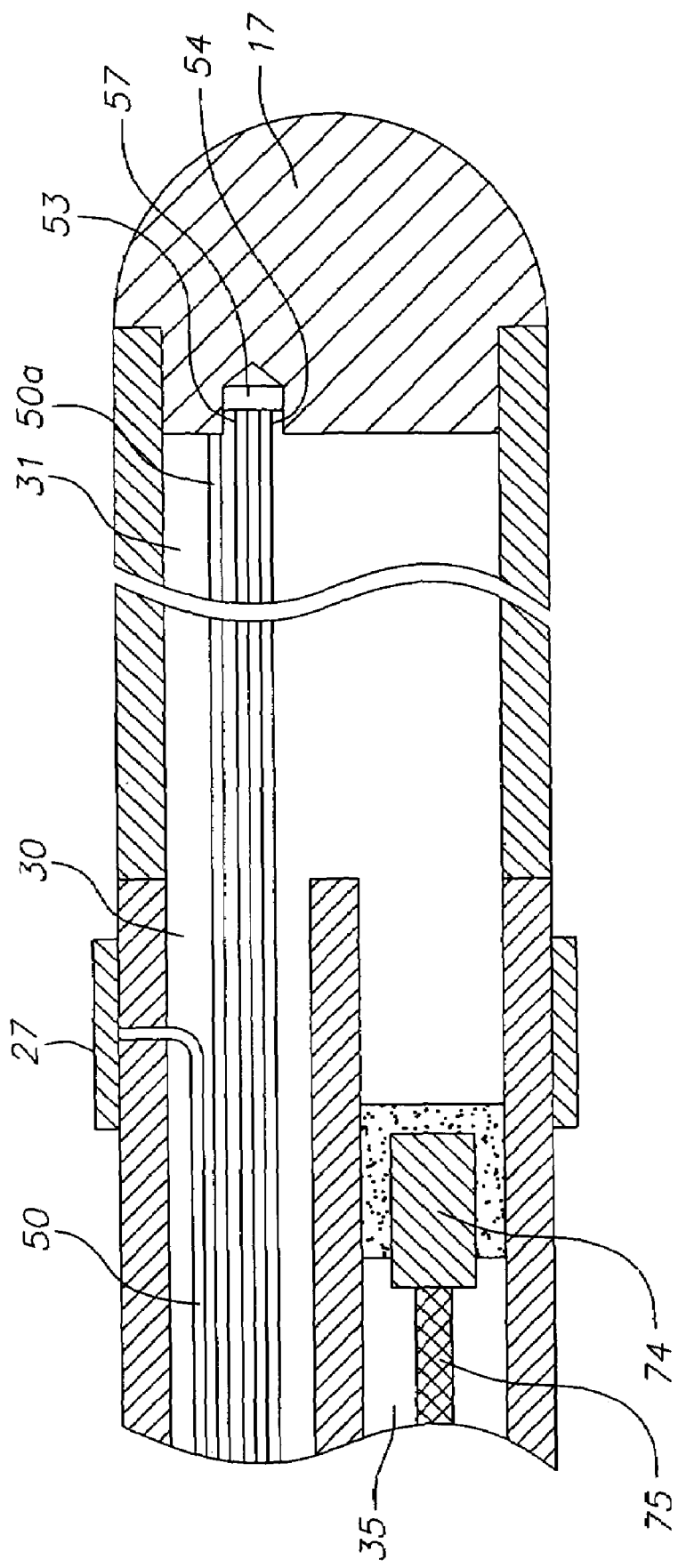
FIG. 4b is a side cross-sectional view, taken of the side opposite that of FIG. 4a, of the tip section of the catheter according to FIG. 4a, including the junction between the intermediate section and the tip section.
Figure 5:
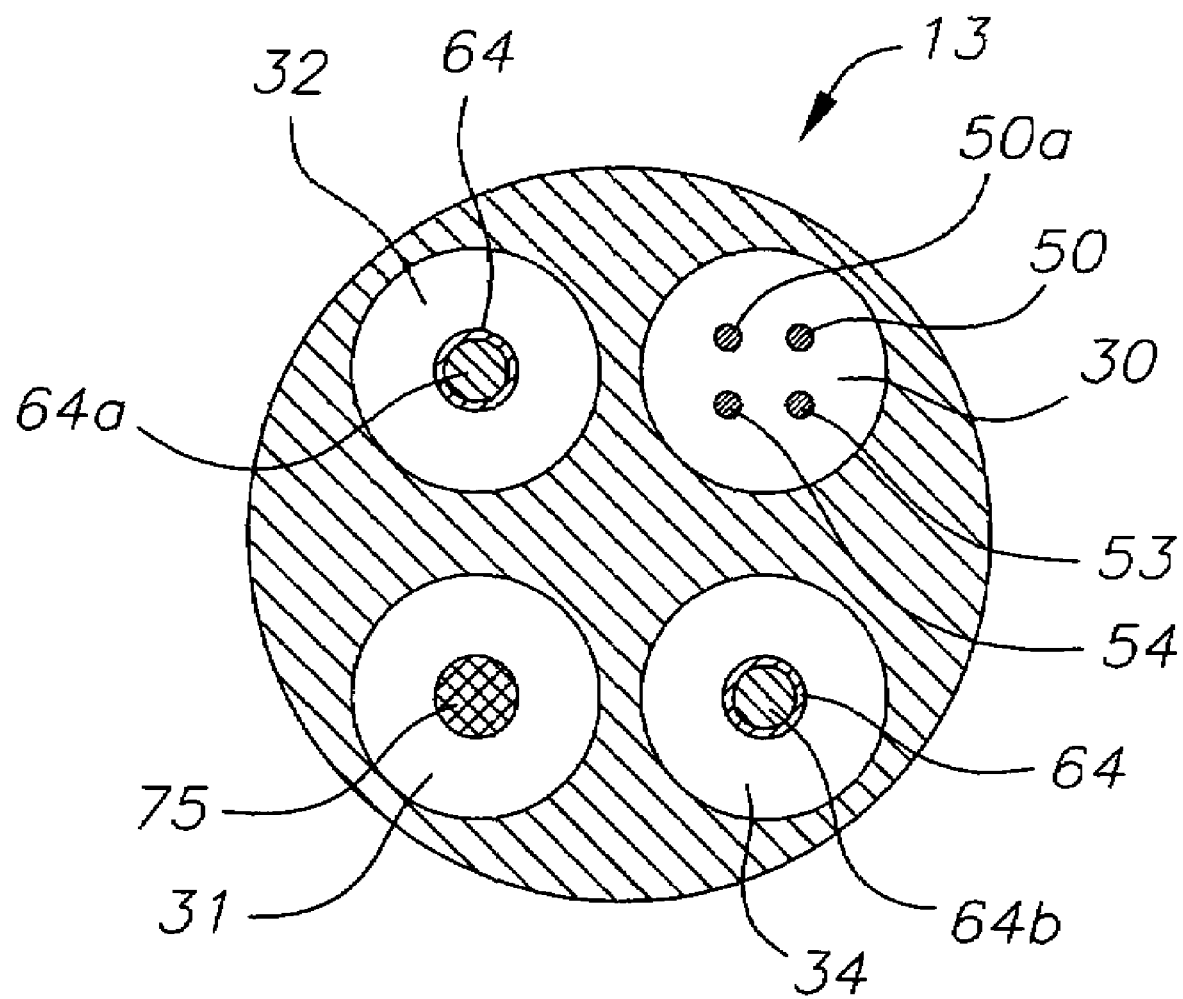
FIG. 5 is a longitudinal cross-sectional view of the intermediate section of FIG. 2a, taken along line 5-5.
Figure 6:
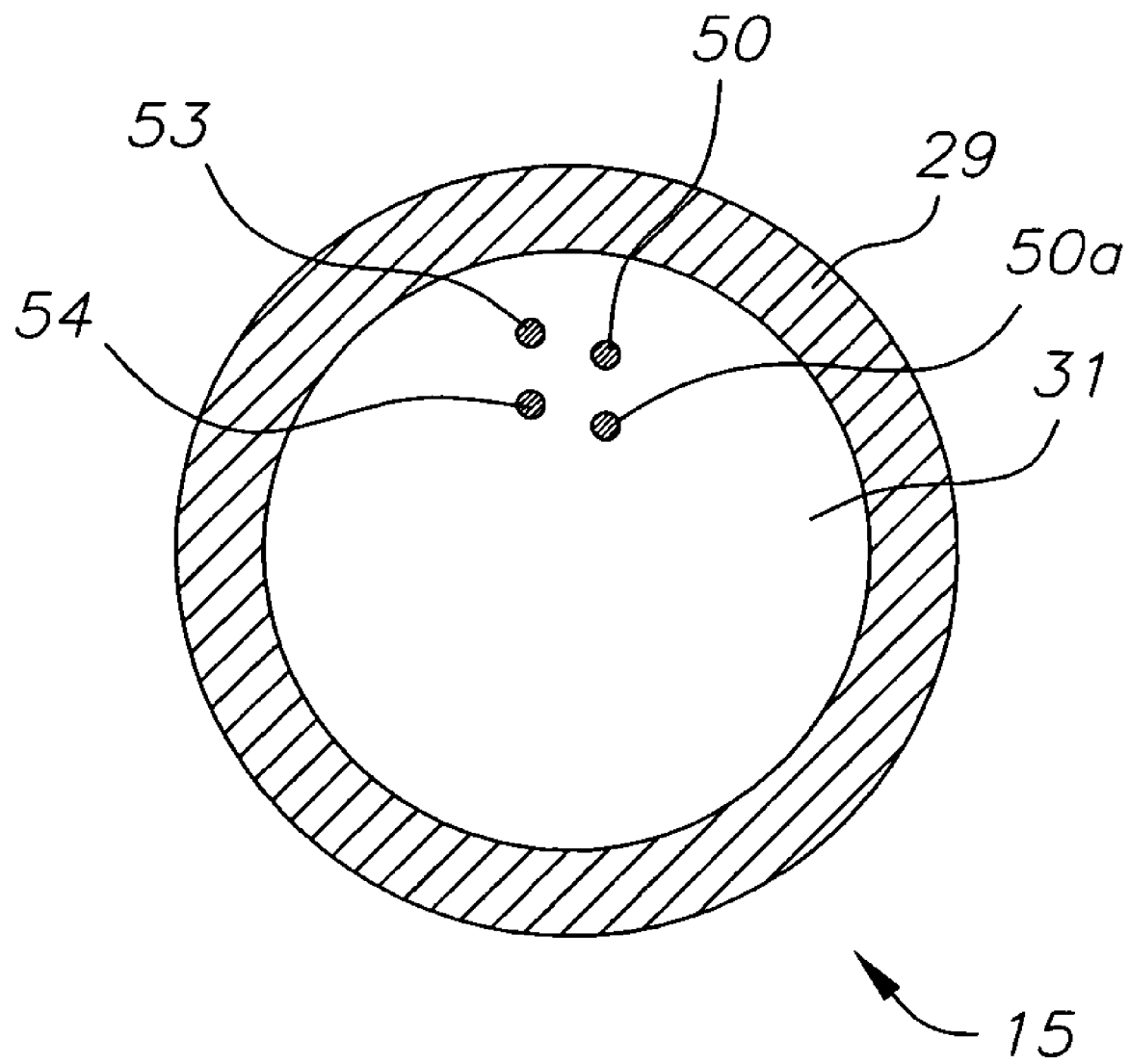
FIG. 6 is a longitudinal cross-sectional view of the tip section of FIG. 4a, taken along line 6-6.

As shown in FIGS. 4a, 4b and 5, the intermediate section 13 comprises a short section of tubing 24 having four lumens 30, 32, 34, and 35. The tubing 24 is made of a suitable non-toxic material and can be more flexible than the catheter body 12. A nonlimiting example of a suitable material for the tubing 24 is braided polyurethane, i.e., polyurethane with an embedded braided mesh of stainless steel or the like. Alternatively, the tubing 24 is made of a suitable silicon, silicone-based or silicone-containing material.

The outer diameter of the intermediate section 13, like that of the catheter body 12, should be no greater than about 8 french. The lumens 30, 32, 34 and 35 each have a diameter ranging from about 0.018 to about 0.020 inch.

Figure 2A:
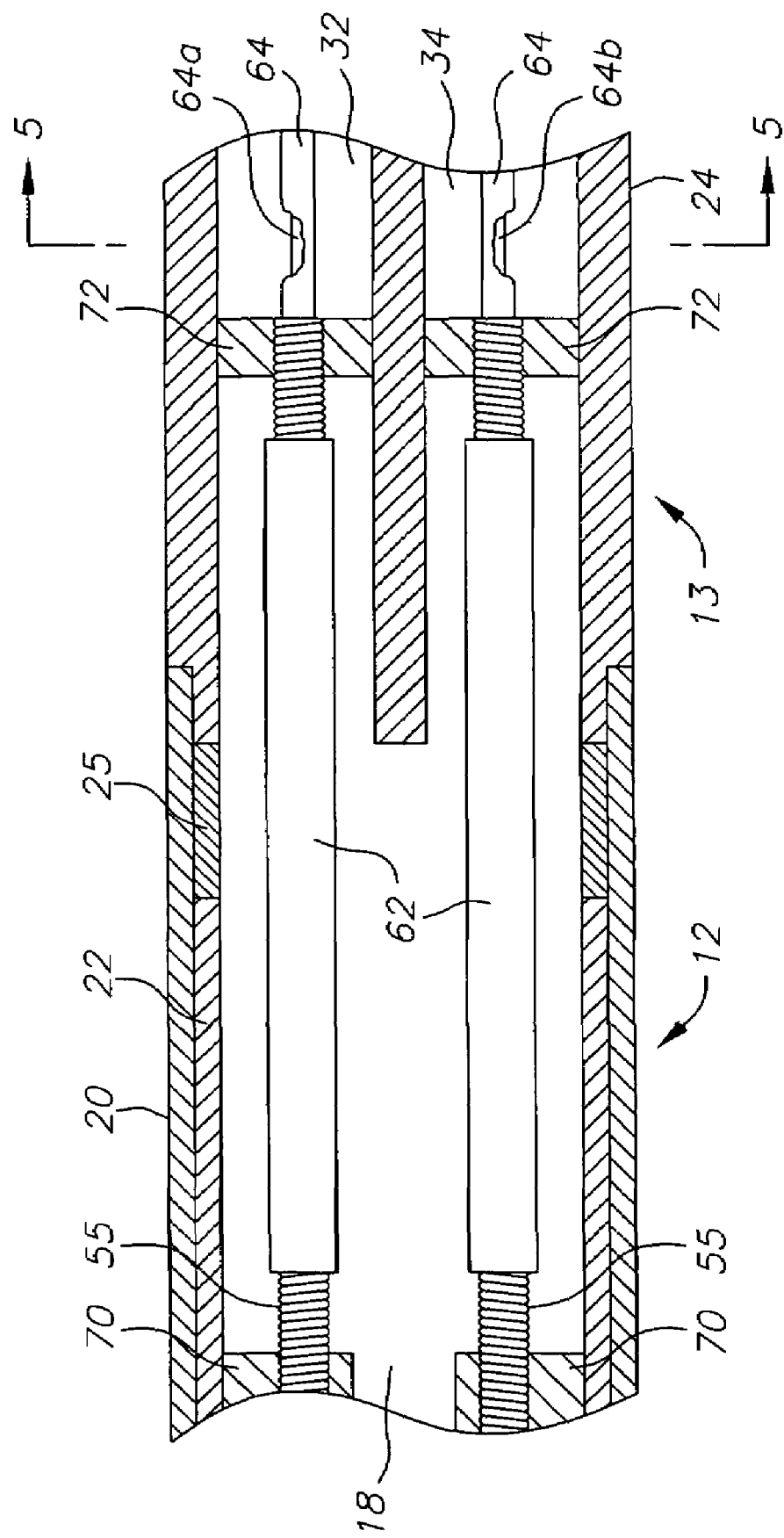
FIG. 2a is a side cross-sectional view of the catheter body according to one embodiment of the present invention, including the junction between the catheter body and intermediate section.
Figure 2B:
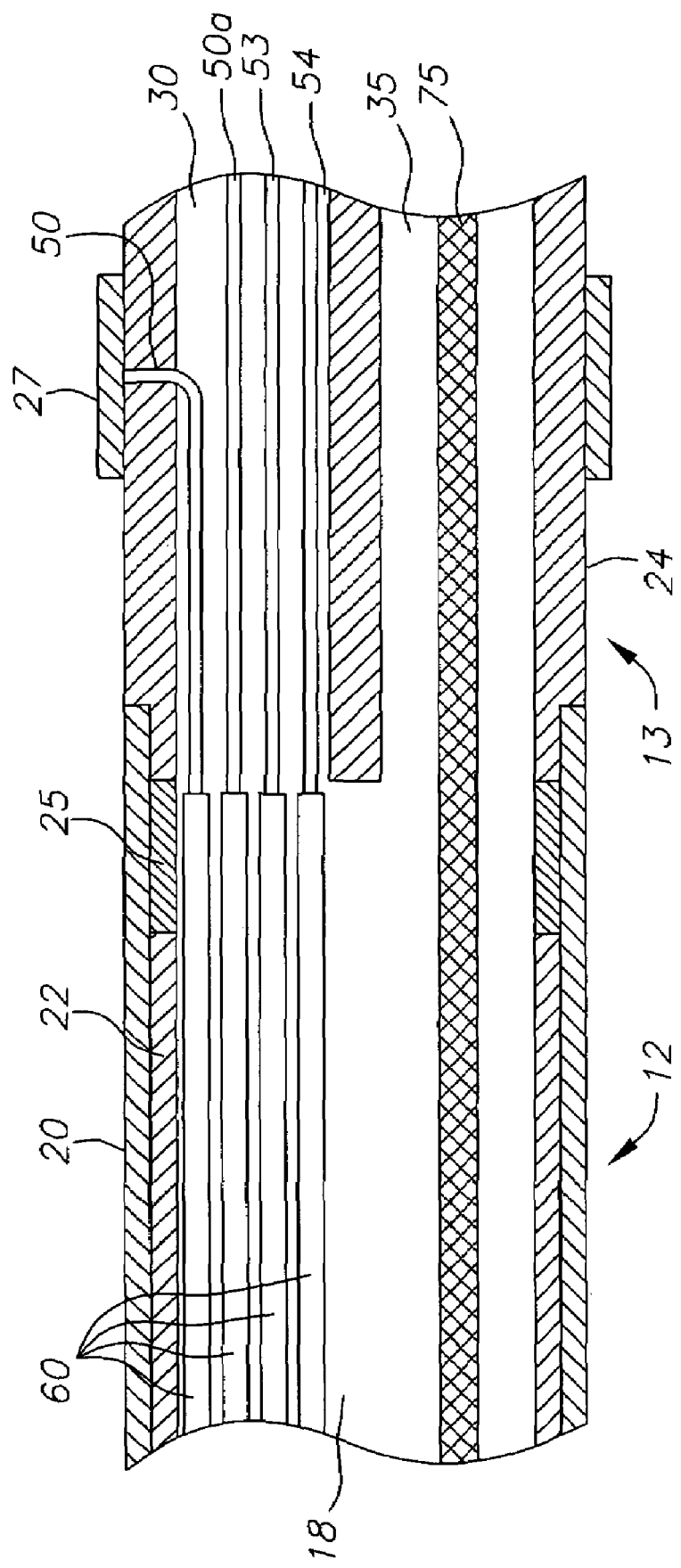
FIG. 2b is a side cross-sectional view, taken of the side opposite that of FIG. 2a, of the catheter body of the catheter of FIG. 2a, including the junction between the catheter body and the intermediate section.

One exemplary means for attaching the catheter body 12 to the intermediate section 13 is illustrated in FIGS. 2a and 2b. The proximal end of the intermediate section 13 comprises an outer circumferential notch 23 that receives the inner surface of the outer wall 20 of the catheter body 12. The intermediate section 13 and catheter body 12 are attached by glue or the like.

In the arrangement shown, a spacer 25 lies within the catheter body 12 between the distal end of the stiffening tube 22 and the proximal end of the intermediate section 13. The spacer 25 can be made of a material that is stiffer than the material of the intermediate section 13, i.e., polyurethane, but not as stiff as the material of the stiffening tube 22, i.e., polyimide. The spacer 25 can also be made of TEFLON® (polytetrafluoroethylene). In one embodiment, the spacer 25 has a length of from about 0.25 inch to about 0.75 inch. In another embodiment, the spacer 25 has a length of about 0.50 inch. The spacer 25 has outer and inner diameters about the same as the outer and inner diameters of the stiffening tube 22. The spacer 25 provides a transition in flexibility at the junction of the catheter body 12 and the intermediate section 13, so that the intermediate section can bend smoothly without folding or kinking.

The length of the intermediate section 13 is not critical. However, the intermediate section 13 should be long enough so that, when the intermediate section 13 is deflected, the entire portion of the esophagus that is close to the ablation site in the left atrium is isolated.

Mounted on the intermediate section 13 is at least one radiopaque marker 27. The at least one radiopaque marker 27 can comprise a plurality of radiopaque markers 27 spanning substantially the length of the intermediate section 13. Alternatively, the at least one radiopaque marker 27 comprises a plurality of radiopaque markers 27 positioned substantially in the center of the intermediate section 13 to enable centering of the intermediate section 13 over the region of the esophagus lying next to the ablation site in the left atrium. The radiopaque markers 27 may comprise ring electrodes made at least partially of a radiopaque material. The radiopaque markers 27 are used to guide the catheter 10 into the esophagus under x-ray or fluoroscopy, and to position the intermediate section 13 over the ablation site.

As noted above, the radiopaque markers 27 may comprise ring electrodes made at least partially of a radiopaque material. In such an embodiment, each ring electrode 27 is connected to a corresponding lead wire 50. Each lead wire 50 extends through the first lumen 30 of the intermediate section 13, through the central lumen 18 of the catheter body 12 and through the control handle 16. The proximal end of each lead wire 50 extends out the proximal end of the control handle 16 and is connected to a suitable monitoring device (not shown). If desired, the portion of each lead wire 50 extending through the catheter body 12 may be enclosed within a non-conductive protective tube or sheath 60.

Each lead wire 50 is connected at its distal end to its corresponding ring electrode 27 by any suitable technique. Each lead wire 50 can be connected to its corresponding ring electrode 27 by first making a small hole through the tubing 24. Such a hole can be created, for example, by inserting a needle through the tubing 24 and heating the needle sufficiently to form a permanent hole. A lead wire 50 is then drawn through the hole by using a microhook or the like. The end of the lead wire 50 is then stripped of any coating and welded to the underside of the ring electrode 27, which is then slid into position over the hole and fixed in place with polyurethane glue or the like.

Mounted at the distal end of the intermediate section 13 is a tip section 15, as shown in FIGS. 4a and 4b. The tip section 15 extends generally along the axis of the catheter body 12. The tip section 15 comprises a segment of flexible tubing 29 having at least one lumen 31, as shown in FIGS. 4a, 4b, and 5. The tubing 29 is made of a suitable non-toxic material that is more flexible than the catheter body 12. A nonlimiting example of a suitable material for the tubing 29 is braided polyurethane, i.e., polyurethane with an embedded mesh of braided stainless steel or the like. Alternatively, the tip section 15 can be made of a silicone, silicone-based or silicone-containing material. The outer diameter of the tip section 15, like that of the intermediate section 13, should be no greater than about 8 french.

The length of the tip section 15 is not critical. However, the tip section 15 should be long enough so that when the longer puller wire 64a is moved longitudinally relative to the catheter body 12, as discussed further below, the tip section 15 does not deflect. Rather, the tip section 15 remains extended generally along the axis of the catheter body 12 so that only the intermediate section 15 deflects, forming a generally C-shaped deflection curve such as that shown in FIGS. 9b and 9c.

In the embodiments shown in FIGS. 4a and 4b, the distal end of the tip section 15 carries a tip electrode 17. The tip electrode 17 and/or the ring electrodes 27 mounted on the intermediate section 13 may be used to measure the proximity of an ablation electrode to the esophagus. This proximity may be measured by any suitable technique, such as impedance, inductance, capacitance, pacing, or location in a magnetic field, as is known in the art.

The tip electrode 17 is connected to a lead wire 50a. In one embodiment, as shown in FIGS. 4a and 4b, the lead wire 50a extends through the lumen 31 of the tip section 15, through the first lumen 30 of the intermediate section, through the central lumen 18 of the catheter body 12 and through the control handle 16. The proximal end of the lead wire 50a extends out the proximal end of the control handle 16 and is connected, either directly or via a connector, to a suitable monitoring device (not shown). If desired, the portion of the lead wire 50a extending through the catheter body 12 may be enclosed within a non-conductive protective tube or sheath 60. As shown in FIGS. 4a and 4b, the portion of the lead wire 50a extending through the tip section 15 may also be enclosed within a non-conductive protective tube or sheath 60.

In one embodiment, as shown in FIGS. 2a, 2b, 3a, 4a, 4b, 5 and 6, the catheter 10 comprises two puller wires 64a and 64b. The first puller wire 64a extends from the control handle 16, through the central lumen 18 in the catheter body 12, and into the second lumen 32 of the intermediate section. The second puller wire 64b extends from the control handle 16, through the central lumen 18 of the catheter body 12, and into the third lumen 34 of the intermediate section 13. As described in more detail below, the proximal end of each puller wire 64a and 64b is anchored within the control handle 16 and the distal end of each puller wire 64a and 64b is anchored within the intermediate section 13.

Each puller wire 64a and 64b is made of any suitable metal, such as stainless steel or Nitinol. In one embodiment, each puller wire 64a and 64b is coated with a coating, such as TEFLON® (polytetrafluoroethylene) or the like. Each puller wire 64a and 64b has a diameter ranging from about 0.006 inch to about 0.010 inch. Both puller wires 64a and 64b can have the same diameter.

Figure 3A:
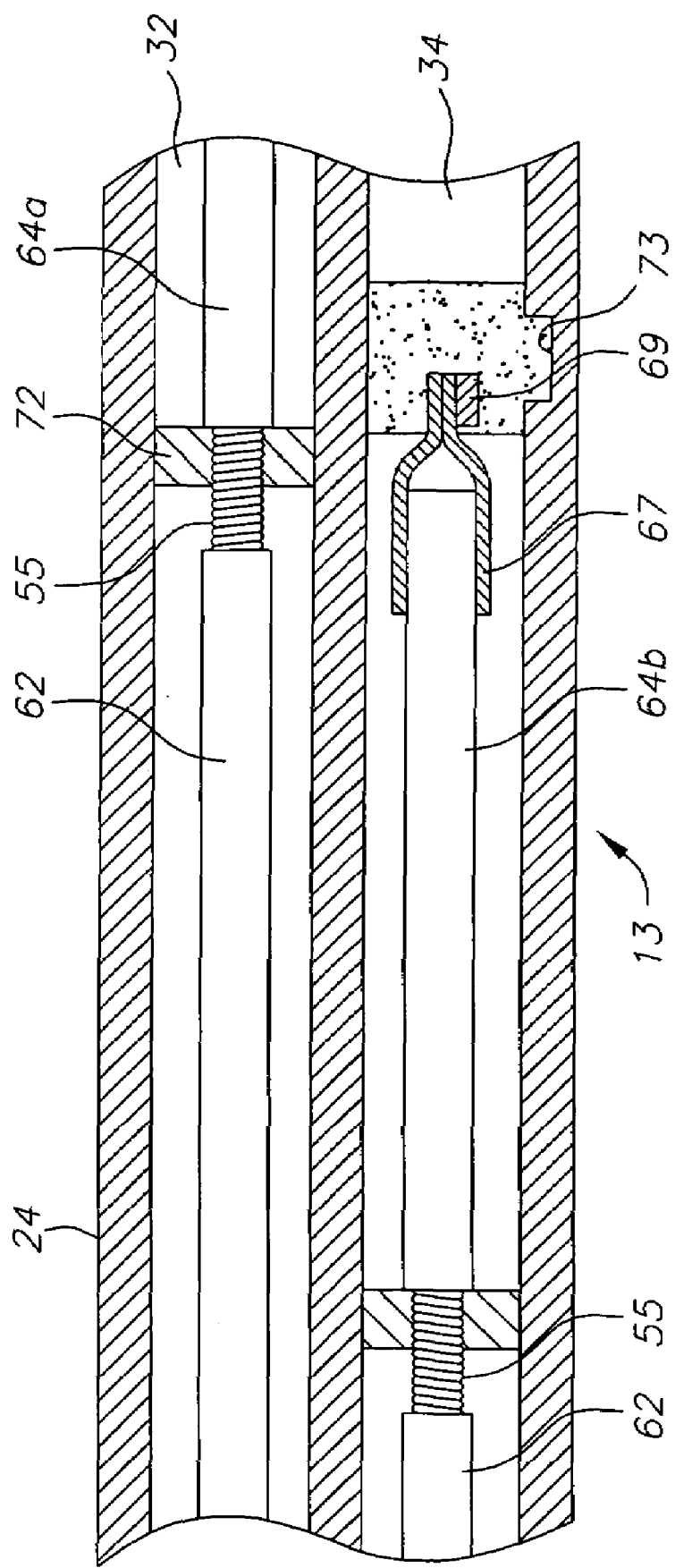
FIG. 3a is a side cross-sectional view of the catheter body according to an alternative embodiment of the present invention, including the junction between the catheter body and intermediate section.
Figure 3B:
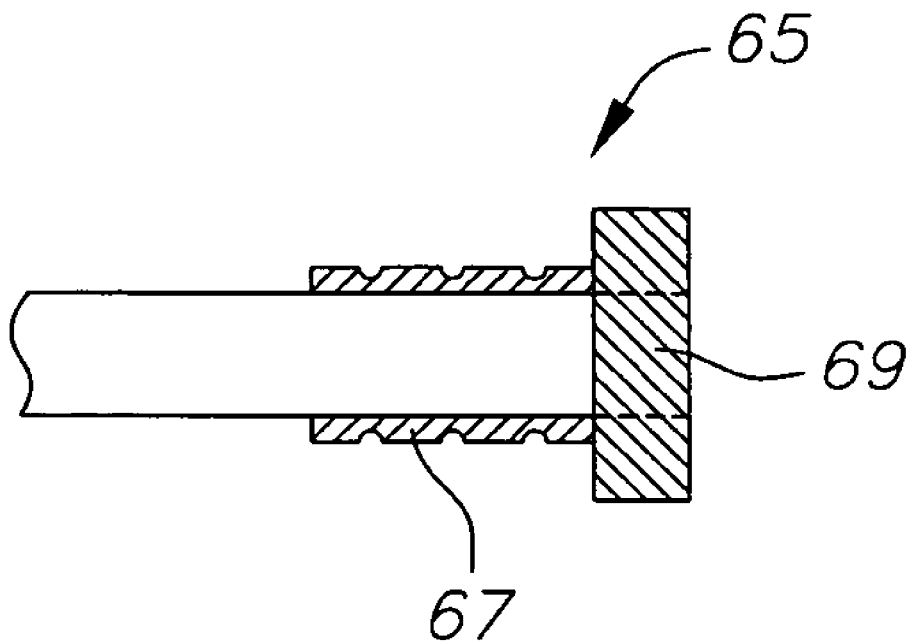
FIG. 3b is a side cross-sectional view of a puller wire anchor according to one embodiment of the present invention.
Figure 3C:
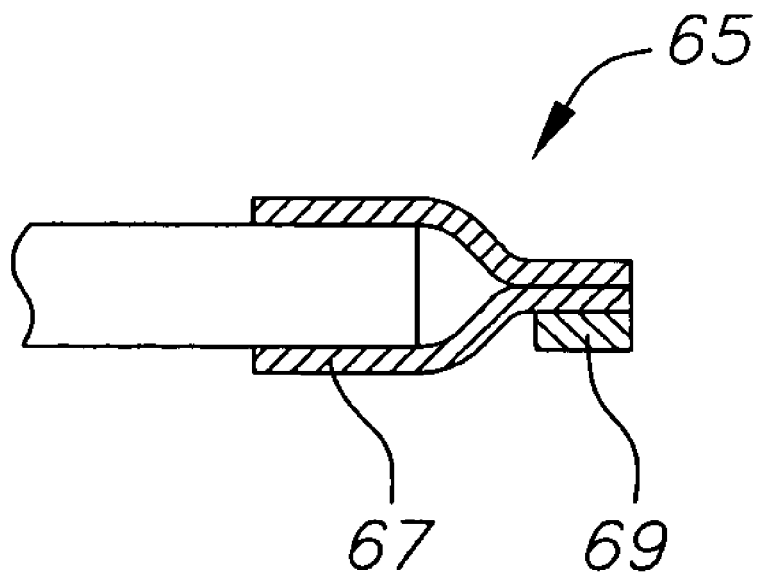
FIG. 3c is a side cross-sectional view of the puller wire anchor of FIG. 3b rotated 90°.

As shown in FIGS. 3a and 4a, the first puller wire 64a is longer than the second puller wire 64b, and is anchored at its distal end to the side wall of the distal end of the intermediate section 13. The second puller wire 64b is shorter than the first puller wire 64a, and is anchored at its distal end to the side wall of the proximal end of the intermediate section 13.

One means for anchoring each puller wire 64a and 64b to the side wall of the intermediate section includes an anchor 65 fixedly attached to the distal end of each puller wire 64a and 64b. In such an embodiment, as shown in FIGS. 3a, 3b, 3c and 4a, the anchor 65 is formed by a metal tube 67, e.g. a short segment of hypodermic stock, that is fixedly attached, e.g. by crimping, to the distal end of the puller wire 64. The tube 67 has a section that extends a short distance beyond the distal end of the puller wire 64a or 64b. A cross-piece 69 made of a small section of stainless steel ribbon or the like is soldered or welded in a transverse arrangement to the distal end of the metal tube 67, which is flattened during the operation. This creates a T-bar anchor 65. A notch 73 is created in the side of the intermediate section 13 resulting in an opening in the corresponding lumen 32 or 34 carrying the puller wire 64a or 64b. The cross piece 69 lies transversely within the notch 73. Because the length of the ribbon forming the cross-piece 69 is longer than the diameter of the opening into the lumen 32 or 34, the anchor 65 cannot be pulled completely into the lumen 32 or 34. The notch 73 is then sealed with polyurethane glue or the like to give a smooth outer surface. The glue flows into the lumen to fully secure the anchor. Other means for anchoring the puller wires 64a and 64b in the intermediate section 13 would be recognized by those skilled in the art and are included within the scope of this invention.

The catheter 10 further comprises two compression coils 55 in surrounding relation to the puller wires 64a and 64b. Each compression coil 55 is made of any suitable metal, such as stainless steel. Each compression coil 55 is tightly wound on itself to provide flexibility, i.e., bending, but to resist compression. The inner diameter of each compression coil 55 is slightly larger than the diameter of its associated puller wire 64a or 64b. For example, when a puller wire 64a or 64b has a diameter of about 0.007 inch, the corresponding compression coil 55 has an inner diameter of about 0.009 inch. The coating on the puller wires 64a and 64b allows them to slide freely within the compression coils 55. The outer surface of each compression coil 55 can be covered along most of its length by a flexible, non-conductive sheath 62 to prevent contact between the compression coil 55 and any wires or cables also dispersed within the central lumen 18 of the catheter body 12. A nonlimiting example of a suitable material for the non-conductive sheath 62 is polyimide tubing.

Each compression coil 55 is anchored at its proximal end to the proximal end of the stiffening tube 22 of the catheter body 12 by a proximal glue joint 70. When a stiffening tube is not used, each compression coil is anchored directly to the outer wall 20 of the catheter body 12. Each compression coil 55 is anchored at its distal end to the proximal end of the intermediate section 13 by distal glue joint 72. Alternatively, the distal end of each compression coil may be anchored to the distal end of the stiffening tube 22 or the distal end of the outer body 20 (when no stiffening tube is used).

The glue joints 70 and 72 comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 and the stiffening tube 22 that is heated sufficiently to form a permanent hole. The glue is then introduced through the hole to the outer surface of the compression coil 55 and wicks around the outer circumference to form a glue joint about the entire circumference of the compression coil 55.

Within the lumens 32 and 34, the puller wires 64a and 64b are surrounded by plastic sheathes 64, which can be made of TEFLON® (polytetrafluoroethylene). The plastic sheathes 64 prevent the puller wires 64a and 64b from cutting into the wall of the intermediate section 13 when the intermediate section 13 is deflected. Alternatively, each puller wire 64a or 64b can be surrounded by a compression coil where the turns are expanded longitudinally, such that the surrounding compression coil is both bendable and compressible.

In the arrangement described above, longitudinal movement of one of the puller wires 64a or 64b in a proximal direction results in deflection of the intermediate section in the direction of the lumen 32 or 34 containing that puller wire. Deflection occurs between the distal end of the compression coil 55 surrounding the puller wire 64a or 64b and the distal anchor site of that puller wire. In the above-described embodiment, proximal movement of the shorter puller wire 64b results in deflection over the proximal half of the intermediate section 13 in the direction of the shorter puller wire 64b. Thereafter, longitudinal movement of the longer puller wire 64a results in deflection of the distal half of the intermediate section 13 in the direction of the lumen housing the longer puller wire 64a.

It should be understood that, if desired, proximal movement of the longer puller wire 64a may occur first followed by proximal movement of the shorter puller wire 64b. However, this sequence is not preferred because the shape and degree of curvature is not as easily controlled.

In an alternative embodiment, as shown in FIG. 3a, the compression coil 55 surrounding the shorter puller wire 64b is anchored at the distal end of the catheter body or proximal end of the intermediate section 13 as described above. In this embodiment, however, the compression coil 55 surrounding the longer puller wire 64a is anchored at about the same position along the length of the intermediate section as the distal anchor site of the shorter puller wire 64b. In this arrangement, proximal movement of the longer puller wire 64a can only result in deflection of the distal portion of the tip section. Therefore, in this embodiment, the sequence in which the puller wires 64a and 64b are manipulated does not matter. It is understood that the anchor sites for the puller wires 64a and 64b may be independently varied as desired.

Longitudinal movement of the puller wires 64a and 64b relative to the catheter body 12, which results in deflection of the intermediate section 13, is accomplished by suitable manipulation of the control handle 16. Nonlimiting examples of suitable control handles 16 for use in the present invention are disclosed in U.S. Pat. Nos. 6,198,974 and 6,468,260, the entire disclosures of which are incorporated herein by reference.

Although the above embodiment is described as including two puller wires 64a and 64b, it is understood that only one puller wire can alternatively be used. In either embodiment, the length of the tip section will ensure that a generally C-shaped curve is obtained upon deflection of the intermediate section.

Figure 7:
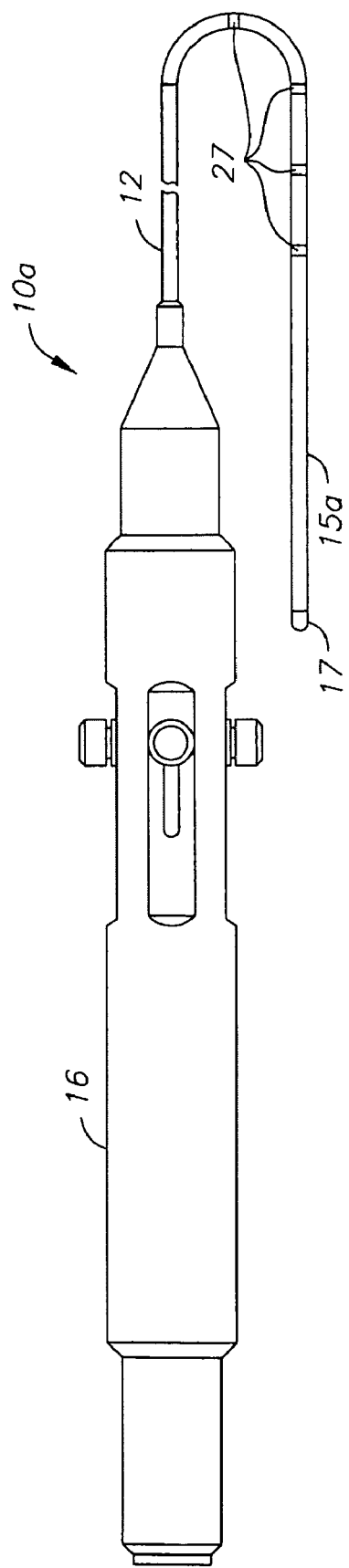
FIG. 7 is an elevated side view of an esophagus isolation catheter according to an alternative embodiment of the present invention.

In an alternative embodiment, as shown in FIG. 7, the catheter 10a comprises an elongated catheter body 12 as described above, and a deflectable tip section 15a. The intermediate section is omitted. The catheter 10a comprises only one puller wire 64 for deflecting the tip section 15a.

As shown in FIGS. 8a, 8b and 8c, the tip section 15a comprises a short section of tubing 29a having four lumens 30a, 32a, 34a, and 35a. The first lumen 30a carries electrode lead wires 50 and 50a. The second lumen 32a carries thermocouple wires 53 and 54. The third lumen 34a carries a puller wire 64. The fourth lumen 35a carries an electromagnetic sensor cable 75.

The tubing 29a is made of a suitable non-toxic material that is more flexible than the catheter body 12. One exemplary material for the tubing 29a is braided polyurethane, i.e., polyurethane with an embedded braided mesh of stainless steel or the like.

The length of the tip section 15a is not critical. However, the tip section 15a should be long enough so that when the puller wire 64 is moved longitudinally relative to the catheter body 12, as discussed further below, the distal section of the tip section 15a, i.e. the section of the tip section distal the anchor point of the puller wire 64, does not deflect. Rather, the distal section of the tip section 15a remains extended generally along the axis of the catheter body 12 so that only the center of the tip section 15a deflects, forming a generally C-shaped deflection curve such as that shown in FIGS. 9b and 9c.

The outer diameter of the tip section 15a, like that of the catheter body 12, is no greater than about 8 french. The lumens 30a, 32a, 34a and 35a each have a diameter of about 0.018 to about 0.020 inch.

One exemplary means for attaching the catheter body 12 to the tip section 15a is illustrated in FIGS. 8a and 8b. The proximal end of the tip section 15a comprises an outer circumferential notch 23a that receives the inner surface of the outer wall 20 of the catheter body 12. The tip section 15a and catheter body 12 are attached by glue or the like.

In the arrangement shown, a spacer 25 lies within the catheter body 12 between the distal end of the stiffening tube 22 and the proximal end of the tip section 15a. The spacer 25 is made of a material that is stiffer than the material of the tip section 15, i.e., polyurethane, but not as stiff as the material of the stiffening tube 22, i.e., polyimide. The spacer 25 can also be made of TEFLON® (polytetrafluoroethylene). One exemplary spacer 25 has a length of from about 0.25 inch to about 0.75 inch. Another exemplary spacer has a length of about 0.50 inch. The spacer 25 has outer and inner diameters about the same as the outer and inner diameters of the stiffening tube 22. The spacer 25 provides a transition in flexibility at the junction of the catheter body 12 and the tip section 15a, so that the tip section 15a can bend smoothly without folding or kinking.

Mounted on the tip section 15a is at least one radiopaque marker 27. The at least one radiopaque marker 27 can comprises a plurality of radiopaque markers 27 spanning substantially the length of the tip section 15a. The radiopaque markers 27 may comprise ring electrodes made at least partially of a radiopaque material. The radiopaque markers 27 are used to guide the catheter 10a into the esophagus E under x-ray or fluoroscopy, and to position the tip section 15a over the ablation site.

As noted above, the radiopaque markers 27 may comprise ring electrodes made at least partially of a radiopaque material. In such an embodiment, each ring electrode 27 is connected to a corresponding lead wire 50. Each lead wire 50 extends through the first lumen 30a of the tip section 15a, through the central lumen 18 of the catheter body 12 and through the control handle 16. The proximal end of each lead wire 50 extends out the proximal end of the control handle 16 and is connected to a suitable monitoring device (not shown). If desired, the portion of each lead wire 50 extending through the catheter body 12 may be enclosed within a non-conductive protective tube or sheath 60.

In the embodiment shown in FIGS. 8a, 8b and 8c, the distal end of the tip section 15a carries a tip electrode 17a. The tip electrode 17a has an atraumatic design so that, when deflected, the tip electrode 17a does not damage the esophagus E. The tip electrode 17a and/or the ring electrodes 27 mounted on the tip section 15a may be used to measure the proximity of an ablation electrode to the esophagus. This proximity may be measured by any suitable technique, such as impedance, inductance, capacitance, pacing, or location in a magnetic field, as is known in the art.

The tip electrode 17a is connected to a lead wire 50a. In one embodiment, as shown in FIGS. 8b and 8c, the lead wire 50a extends through the first lumen 30a of the tip section 15a, through the central lumen 18 of the catheter body 12 and through the control handle 16. The proximal end of the lead wire 50a extends out the proximal end of the control handle 16 and is connected, either directly or via a connector, to a suitable monitoring device (not shown). If desired, the portion of the lead wire 50a extending through the catheter body 12 may be enclosed within a non-conductive protective tube or sheath 60.

In this embodiment, the catheter 10a comprises a single puller wire 64. As shown in FIG. 8a, the puller wire 64 extends from the control handle 16, through the central lumen 18 of the catheter body 12, and into the second lumen 32a of the tip section 15a. The proximal end of the puller wire 64 is anchored within the control handle 16 and the distal end of the puller wire 64 is anchored within the tip section 15a. The distal end of the puller wire 64 is anchored near the center of the tip section 15a by any suitable means, for example, by the means described above.

The puller wire 64 is made of any suitable metal, such as stainless steel or Nitinol. The puller wire 64 can be coated with a coating, such as TEFLON® (polytetrafluoroethylene) or the like. The puller wire 64 has a diameter ranging from about 0.006 inch to about 0.010 inch.

The catheter 10 further comprises a compression coil 55a in surrounding relation to the puller wire 64. The compression coil 55a is made of any suitable metal, such as stainless steel. The compression coil 55a is tightly wound on itself to provide flexibility, i.e., bending, but to resist compression. The inner diameter of the compression coil 55a is slightly larger than the diameter of the puller wire 64. For example, when the puller wire 64 has a diameter of about 0.007 inch, the compression coil 55a has an inner diameter of about 0.009 inch. The coating on the puller wire 64 allows it to slide freely within the compression coil 55a. The outer surface of the compression coil 55a can be covered along most of its length by a flexible, non-conductive sheath 62 to prevent contact between the compression coil 55a and any wires or cables also dispersed within the central lumen 18 of the catheter body 12. The non-conductive sheath 62 can be made of polyimide tubing.

The compression coil 55a is anchored at its proximal end to the proximal end of the stiffening tube 22 of the catheter body 12 by a proximal glue joint 70. When a stiffening tube is not used, the compression coil is anchored directly to the outer wall 20 of the catheter body 12. The compression coil 55a is anchored at its distal end to the proximal end of the tip section 15a by distal glue joint 72. Alternatively, the distal end of the compression coil 55a may be anchored to the distal end of the stiffening tube 22 or the distal end of the outer body 20 (when no stiffening tube is used).

Within the second lumen 32a of the tip section 15a, the puller wire 64 is surrounded by a plastic sheath 62, which can be made of TEFLON® (polytetrafluoroethylene). The plastic sheath 62 prevents the puller wire 64 from cutting into the wall of the tip section 15a when the tip section 15a is deflected. Alternatively, the puller wire 64 can be surrounded by a compression coil where the turns are expanded longitudinally, such that the surrounding compression coil is both bendable and compressible.

Longitudinal movement of the puller wire 64, resulting in deflection of the tip section 15a and the esophagus E, is accomplished by suitable manipulation of the control handle 16. Nonlimiting examples of control handles suitable for use with this embodiment of the present invention include those described in U.S. Pat. Nos. Re 34,502 and 5,897,529, the entire disclosures of which are incorporated herein by reference.

Although this embodiment is described as including a single puller wire 64, it is understood that two puller wires can alternatively be used, as described above with respect to the intermediate section embodiment. In either embodiment, the length of the distal section of the tip section will ensure that a generally C-shaped curve is obtained upon deflection.

One or more temperature sensors may be provided along the length of the catheter body 12 to monitor the temperature of the esophageal tissue. The temperature sensors may be attached to the tip electrode and/or ring electrodes. Monitoring the temperature of the esophageal tissue allows the physician to control power delivery to an ablation electrode during ablation in order to prevent thermal damage to the esophagus. In one embodiment, at least one temperature sensor is mounted in the intermediate section. In an alternative embodiment, a plurality of temperature sensors are mounted along substantially the entire length of the intermediate section or tip section, in order to monitor the temperature of the esophageal tissue lying along the entire ablation site.

Any conventional temperature sensors, e.g. thermocouples or thermistors, may be used. In the embodiments shown in FIGS. 4b, 5, 6, 8a and 8c, the temperature sensors comprise thermocouples formed by enameled wire pairs. One wire of each wire pair is a copper wire 53, e.g. a number 40 copper wire. The other wire of each wire pair is a constantan wire 54. The wires 53 and 54 of each wire pair are electrically isolated from each other except at their distal ends where they are twisted together, covered with a short piece of plastic tubing 57, e.g. polyimide, and covered with epoxy. The plastic tubings 57 are anchored to the side wall of the intermediate section 13 or tip section 15a by glue or the like. The temperature sensors may be anchored anywhere along the length of the tip section 15a or intermediate section 13 such that the temperature of the esophageal tissue can be monitored. In one embodiment, as shown in FIGS. 2b, 4b, 5 and 6, the wires 53 and 54 extend through the first lumen 30 of the intermediate section 13, through the central lumen 18 of the catheter body 12, and out through the control handle 16 to a connector (not shown) connectable to a temperature monitor (not shown).

As noted above with respect to the lead wires 50 and 50a, the portion of the wires 53 and 54 extending through the catheter body 12 may be encased within a protective sheath 60. The protective sheath 60 can be made of any suitable material, for example polyimide. The protective sheath 60 is anchored at its distal end to the side wall of the catheter body 12 by gluing it to the side wall with polyurethane glue or the like.

An electromagnetic sensor 74 may be contained within the intermediate section 13, as shown in FIG. 4b, or tip section 15a, as shown in FIGS. 8b and 8c. In the embodiment with an intermediate section 13, the electromagnetic sensor 74 is anchored in the center of the intermediate section 13. The electromagnetic sensor 74 is anchored to the side wall of the intermediate section 13 or tip section 15a by any suitable means, e.g., by polyurethane glue or the like. The electromagnetic sensor 74 may be used to ensure that the deflectable intermediate section 13 or tip section 15a is positioned in the esophagus at the location where the esophagus lies next to the ablation site. The electromagnetic sensor 74 may also be used to determine the proximity of the esophagus to an ablation electrode, as is known in the art.

The electromagnetic sensor 74 is connected to an electromagnetic sensor cable 75, which, in one embodiment, as shown in FIGS. 2b, 4b and 5, extends through the fourth lumen 35 of the intermediate section 13, through the central lumen 18 of the catheter body 12, and out through the control handle 16. In an alternative embodiment, as shown in FIGS. 8b and 8c, the electromagnetic sensor cable 75 extends through the fourth lumen 35a of the tip section 15a, through the central lumen 18 of the catheter body 12, and out through the control handle 16.

The electromagnetic sensor cable 75 comprises multiple wires encased within a plastic covered sheath. In the control handle 16, the sensor cable 75 is connected to a circuit board (not shown). The circuit board amplifies the signal received from the electromagnetic sensor 74 and transmits it to a computer in a form understandable by the computer. Because the catheter 10 is designed for a single use only, the circuit board may contain an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443,489, 5,480, 422, 5,546,951 and 5,391,199, the entire disclosures of which are incorporated herein by reference.

Figure 9B:
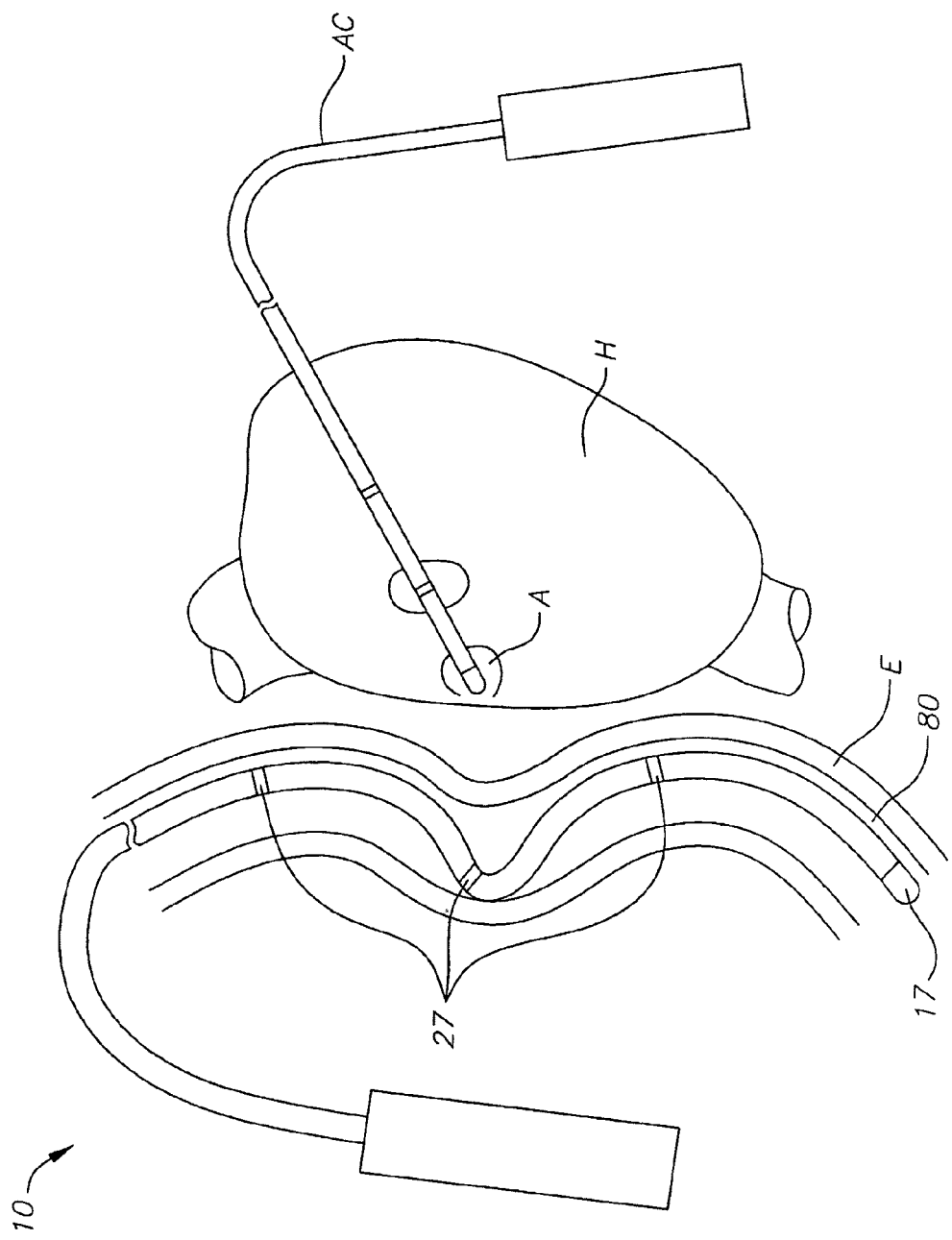
Figure 9C:
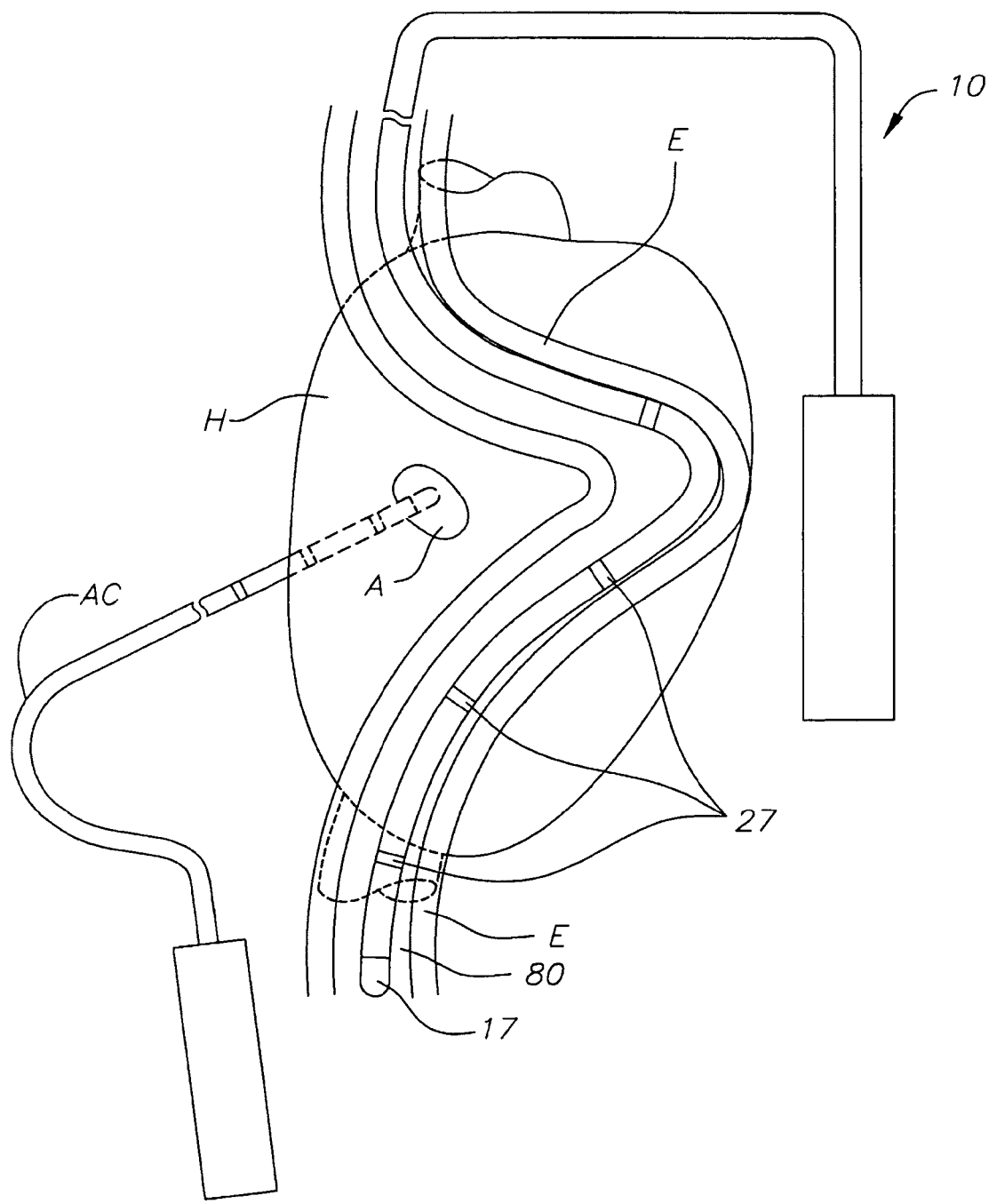

In use, the catheter 10 is inserted into an esophagus E of a patient. The catheter 10 may be introduced into the esophagus either through the throat or nasal passage of the patient, and may be introduced either directly or within a gastric tube 80, as shown in FIGS. 9a, 9b and 9c. The radiopaque markers 27 on the intermediate section 13 or tip section 15a of the catheter 10 provide a visual reference of the location of the esophagus E relative to the desired ablation site A in the left atrium of the heart H. Prior to initiating left atrial ablation with an ablation catheter AC, the position of the esophagus E is recorded by imaging the intermediate section 13 by x-ray. The radiopaque markers 27 of the intermediate section 13 are then centered over the ablation site A. The intermediate section 13 is then deflected by manipulation of the control handle 16.

Deflection of the intermediate section 13 physically moves the esophagus E away from the ablation site A. The direction of deflection relative to the left atrium may be either posterior, as shown in FIG. 9b, or lateral, as shown in FIG. 9c. Posterior deflection of the esophagus E lifts the esophagus off of the posterior wall of the left atrium. Lateral deflection of the esophagus E moves the esophagus E along the posterior wall of the left atrium, but directs the esophagus E away from the ablation site A.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. An esophagus isolation catheter adapted for use within a patient's esophagus, the esophagus isolation catheter comprising:
    an elongated catheter body having an axis, and at least one lumen therethrough;
    a deflectable section distal the catheter body and comprising a single elongated tubing;
    an elongated tip section distal the deflectable section and extending generally along the axis of the catheter body; and
    means for deflecting a region of the patient's esophagus about the deflectable section comprising a puller wire having a distal end anchored near a center of the elongated tip section and distanced from a distal end of the elongated tip section, wherein a length of the elongated tip section is such that longitudinal movement of the puller wire relative to the catheter body results in deflection of the deflectable section to form a generally C-shaped curve having an outer wall that displaces the region of the esophagus to be deflected while the elongated tip section extends undeflected in the esophagus without displacing a region of the esophagus distal the deflectable section before, during and after deflection.

2. An esophagus isolation catheter according to claim 1, further comprising a tip electrode at the distal end of the tip section.

3. An esophagus isolation catheter adapted for use within a patient's esophagus, the esophagus isolation catheter comprising:
    an elongated catheter body having an axis, and at least one lumen therethrough;
    a deflectable section distal the catheter body;
    an elongated tip section distal the deflectable section and extending generally along the axis of the catheter body; and
    means for deflecting a region of the patient's esophagus about the deflectable section comprising:
        a first puller wire having proximal and distal ends, the distal end of the first puller wire being anchored near a distal end of the deflectable section and distanced from a distal end of the elongated tip section;
        a second puller wire shorter than the first puller wire and having proximal and distal ends, the distal end of the second puller wire being anchored near a proximal end of the deflectable section and distanced from the distal end of the elongated tip section; and
        a control handle, wherein the proximal ends of the first and second puller wires are anchored within the control handle;
    whereby longitudinal movement of the first and second puller wires results in deflection of the deflectable section to form a generally C-shaped curve having an outer wall that displaces the region of the esophagus to be deflected while the elongated tip section extends undeflected in the esophagus without displacing a region of the esophagus distal the deflectable section before, during and after deflection.

4. An esophagus isolation catheter according to claim 3, further comprising:
    a first compression coil in surrounding relation to the first puller wire, the first compression coil having proximal and distal ends, the distal end of the first compression coil being anchored in a proximal end of the catheter body; and
    a second compression coil in surrounding relation to the second puller wire, the second compression coil having proximal and distal ends, the distal end of the second compression coil being anchored in the proximal end of the catheter body.

5. An esophagus isolation catheter according to claim 4, wherein deflection of the deflectable section in a generally C-shaped curve is accomplished by first moving the second puller wire longitudinally relative to the catheter body and thereafter moving the first puller wire longitudinally relative to the catheter body.

6. An esophagus isolation catheter according to claim 3, further comprising:
    a first compression coil in surrounding relation to the first puller wire, the first compression coil having proximal and distal ends, the distal end of the first compression coil being anchored in the deflectable section at the anchor site of the second puller wire; and
    a second compression coil in surrounding relation to the second puller wire, the second compression coil having proximal and distal ends, the distal end of the second compression coil being anchored in the proximal end of the catheter body.

7. An esophagus isolation catheter according to claim 6, wherein deflection of the deflectable section in a generally C-shaped curve is accomplished by first moving the second puller wire longitudinally relative to the catheter body and thereafter moving the first puller wire longitudinally relative to the catheter body.

8. An esophagus isolation catheter according to claim 6, wherein deflection of the deflectable section in a generally C-shaped curve is accomplished by first moving the first puller wire longitudinally relative to the catheter body and thereafter moving the second puller wire longitudinally relative to the catheter body.

9. An esophagus isolation catheter according to claim 1, wherein the distal end of the tip section carries a tip electrode, the tip electrode having an atraumatic design for preventing damage to the esophagus upon deflection.

10. An esophagus isolation catheter according to claim 1, wherein the means for deflecting the deflectable section further comprises:
    a control handle, wherein the proximal end of the puller wire is anchored within the control handle.

11. An esophagus isolation catheter according to claim 1, further comprising at least one radiopaque marker mounted on the deflectable section.

12. An esophagus isolation catheter according to claim 1, further comprising a plurality of radiopaque markers mounted on the deflectable section spanning substantially the length of the deflectable section.

13. An esophagus isolation catheter according to claim 11, wherein the radiopaque marker comprises a ring electrode at least partially comprising a radiopaque material.

14. An esophagus isolation catheter according to claim 12, wherein the radiopaque markers each comprise a ring electrode at least partially comprising a radiopaque material.

15. An esophagus isolation catheter according to claim 1, further comprising means for monitoring the temperature of esophageal tissue.

16. An esophagus isolation catheter according to claim 15, wherein the means for monitoring the temperature of esophageal tissue comprises at least one temperature sensor mounted on one or more of the catheter body and deflectable section.

17. An esophagus isolation catheter according to claim 1, further comprising an electromagnetic sensor mounted within the deflectable section.

18. An esophagus isolation catheter adapted for use within a patient's esophagus, the esophagus isolation catheter comprising:
   an elongated catheter body having an axis, and at least one lumen therethrough;
   an intermediate section having proximal and distal ends distal the catheter body,
   an elongated tip section distal the intermediate section and extending generally along the axis of the catheter body;
   a first puller wire having proximal and distal ends, the distal end of the first puller wire being anchored near the distal end of the intermediate section and distanced from a distal end of the elongated tip section;
   a second puller wire shorter than the first puller wire and having proximal and distal ends, the distal end of the second puller wire being anchored near the proximal end of the intermediate section and distanced from the distal end of the elongated tip section; and
   a control handle, wherein the proximal ends of the first and second puller wires are anchored within the control handle;
   wherein a length of the elongated tip section is such that longitudinal movement of the first and second puller wires results in deflection of the intermediate section in a generally C-shaped curve having an outer wall that displaces the region of the esophagus to be deflected while the tip section extends undeflected in the esophagus without displacing a region of the esophagus distal the deflectable section before, during and after deflection.

19. An esophagus isolation catheter according to claim 18, further comprising a tip electrode at the distal end of the tip section.

20. An esophagus isolation catheter according to claim 18, further comprising:
   a first compression coil in surrounding relation to the first puller wire, the first compression coil having proximal and distal ends, the distal end of the first compression coil being anchored in a proximal end of the catheter body; and
   a second compression coil in surrounding relation to the second puller wire, the second compression coil having proximal and distal ends, the distal end of the second compression coil being anchored in the proximal end of the catheter body.

21. An esophagus isolation catheter according to claim 20, wherein deflection of the intermediate section in a generally C-shaped curve is accomplished by first moving the second puller wire longitudinally relative to the catheter body and thereafter moving the first puller wire longitudinally relative to the catheter body.

22. An esophagus isolation catheter according to claim 18, further comprising:
   a first compression coil in surrounding relation to the first puller wire, the first compression coil having proximal and distal ends, the distal end of the first compression coil being anchored in the intermediate section at the anchor site of the second puller wire; and
   a second compression coil in surrounding relation to the second puller wire, the second compression coil having proximal and distal ends, the distal end of the second compression coil being anchored in a proximal end of the catheter body.

23. An esophagus isolation catheter according to claim 22, wherein deflection of the intermediate section in a generally C-shaped curve is accomplished by first moving the second puller wire longitudinally relative to the catheter body and thereafter moving the first puller wire longitudinally relative to the catheter body.

24. An esophagus isolation catheter according to claim 22, wherein deflection of the intermediate section in a generally C-shaped curve is accomplished by first moving the first puller wire longitudinally relative to the catheter body and thereafter moving the second puller wire longitudinally relative to the catheter body.

25. An esophagus isolation catheter adapted for use within a patient's esophagus, the esophagus isolation catheter comprising:
   an elongated catheter body having an axis, and at least one lumen therethrough;
   a tip section having proximal and distal regions distal the catheter body, the tip section being more flexible than the catheter body;
   a puller wire having proximal and distal ends, the distal end of the puller wire being anchored in the proximal region of the tip section distanced from a distal end of the tip section; and
   a control handle, wherein the proximal end of the puller wire is anchored within the control handle;
   wherein a length of the distal region of the tip section is such that longitudinal movement of the puller wire results in deflection of the proximal region of the tip section in a generally C-shaped curve having an outer wall that displaces the region of the esophagus to be deflected while the distal region of the tip section extends undeflected in the esophagus without displacing a region of the esophagus distal the proximal region of the tip section before, during and after deflection.

26. An esophagus isolation catheter according to claim 25, wherein the distal region of the tip section carries a tip electrode, the tip electrode having an atraumatic design for preventing damage to the esophagus upon deflection.

27. A method of deflecting an esophagus of a patient away from an ablation site in the left atrium of the patient's heart, the method comprising:
   introducing the catheter of claim 1 into the esophagus of the patient;

positioning the deflectable section of the catheter in a region of the esophagus corresponding to the ablation site in the patient's left atrium; and deflecting the deflectable section of the catheter.

28. A method of deflecting an esophagus of a patient away from an ablation site in the left atrium of the patient's heart, the method comprising:

introducing the catheter of claim 18 into the esophagus of the patient;

positioning the intermediate section of the catheter in a region of the esophagus corresponding to the ablation site in the patient's left atrium; and deflecting the deflectable section of the catheter.

29. A method of deflecting an esophagus of a patient away from an ablation site in the left atrium of the patient's heart, the method comprising:

introducing the catheter of claim 25 into the esophagus of the patient;

positioning the proximal region of the tip section of the catheter in a region of the esophagus corresponding to the ablation site in the patient's left atrium; and deflecting the deflectable section of the catheter.

30. A method of deflecting an esophagus of a patient away from an ablation site in the left atrium of the patient's heart, the method comprising:

introducing the catheter of claim 11 into the esophagus of the patient;

positioning the deflectable section of the catheter in a region of the esophagus corresponding to the ablation site in the patient's left atrium using the radiopaque markers on the deflectable section; and deflecting the deflectable section of the catheter.

31. A method of deflecting an esophagus of a patient away from an ablation site in the left atrium of the patient's heart, the method comprising:

introducing the catheter of claim 12 into the esophagus of the patient;

positioning the deflectable section of the catheter in a region of the esophagus corresponding to the ablation site in the patient's left atrium using the radiopaque markers on the deflectable section; and deflecting the deflectable section of the catheter.

* * * * *

UNITED STATES PATENT AND TRADEMARK OFFICE
CERTIFICATE OF CORRECTION

Page 1 of 1

PATENT NO.         : 8,273,016 B2
APPLICATION NO.    : 11/372665
DATED              : September 25, 2012
INVENTOR(S)        : Martin F. O'Sullivan It is certified that error appears in the above-identified patent and that said Letters Patent is hereby corrected as shown below:

In the Claims

Column 13, Claim 3, line 58

After "section"
Insert -- comprising a single elongated tubing --

Column 15, Claim 18, line 31

After "body,"
Insert -- the intermediate section being more flexible than the catheter body --

Signed and Sealed this
Fifteenth Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,273,016 B2 | Page 1 of 1 |
| APPLICATION NO. | : 11/372665 | |
| DATED | : September 25, 2012 | |
| INVENTOR(S) | : O'Sullivan | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 687 days.

Signed and Sealed this
Twenty-sixth Day of August, 2014

Michelle K. Lee
*Deputy Director of the United States Patent and Trademark Office*